April 3, 1956 E. S. BOERNER Plant Pat. 1,467
CHRYSANTHEMUM PLANT
Filed May 18, 1955
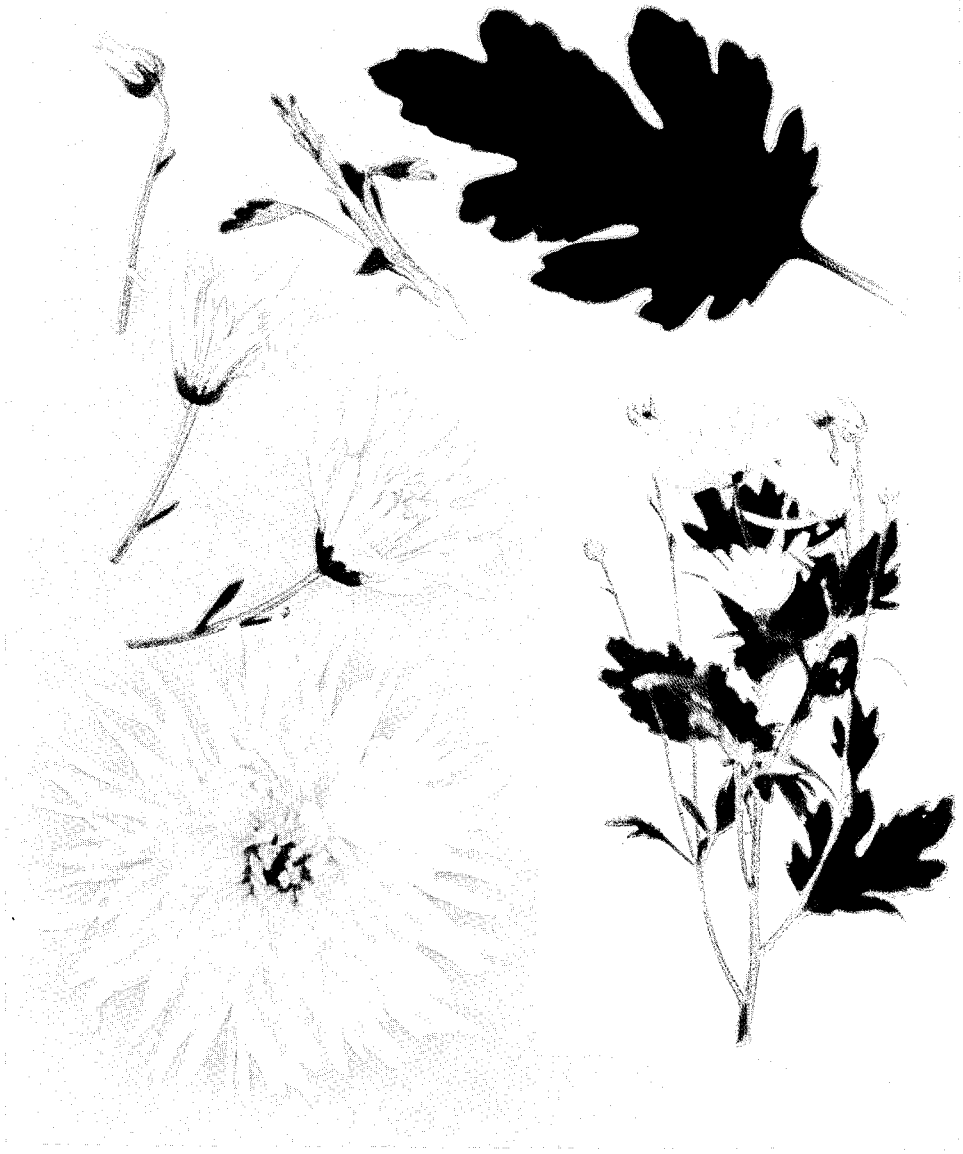
Inventor.
E. S. Boerner
By: Robb & Robb
Attorneys.

United States Patent Office

Plant Pat. 1,467
Patented Apr. 3, 1956

1,467

CHRYSANTHEMUM PLANT

Eugene S. Boerner, Newark, N. Y., assignor to Jackson & Perkins Company, Newark, N. Y., a corporation of New York Application May 18, 1955, Serial No. 509,437

1 Claim. (Cl. 47—60)

The present invention relates to a new and distinct variety of chrysanthemum plant of the decorative class which was originated by me by crossing the variety "September Dawn" (unpatented) with the variety "Mrs. Du Pont" (unpatented).

The primary objective of this cross was to produce a new chrysanthemum variety which combines the hardiness, floriferousness and flower form of the parent variety "September Dawn," with the same or better flower color of the parent variety "Mrs. Du Pont." This objective was fully achieved, along with other improved features of the new variety, as evidenced by the following outstanding characteristics with which the new variety is endowed:

(1) The very compact habit of growth and good winter hardiness of the plant;

(2) The very healthy, deep Green foliage which remains on the plant all the way to the ground;

(3) The stiff, upright stems;

(4) The good productivity, large size, decorative form and good frost resistance of the flowers; and (5) The distinctive Light Orange Yellow, lightly overcast with Capucine Yellow, general color tonality of the flowers.

The foregoing characteristics and distinctions definitely differentiate my new variety from its parents, as well as from all other varieties of its class of which I am aware, and asexual reproduction of the new variety by both top cuttings and underground runners, as performed by me at Newark, New York, shows that these characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: "September Dawn" X "Mrs. Du Pont."
Classification: Decorative.
Growth: From 32 inches to 36 inches; compact.

Cold resistance: Very winter hardy in Northern New York; frost resistant flowers.

Blooming period: In the Newark, New York, climatic area, blooming starts about September 15 and continues until freezing weather.

FLOWER (Observations made from specimens grown in a field at Newark, New York, in the early morning in the early part of October.)

Bud:

*Color.*—When sepals first divide—Baryta Yellow, Plate 4. When petals begin to unfurl—Orange Buff, Plate 3. When half blown: inside of petal—Light Orange Yellow, Plate 3; reverse of petal—Buff Yellow, Plate 4.

*Peduncle.* — Strength — strong. Color — Absinthe Green, Plate 31.

Bloom:

*Size.*—From 3½ inches to 4 inches.

*Stem.*—Strong; stiff; upright.

*Form.*—Decorative.

*Petalage.*—Double.

*Color.*—Center of flower—Mikado Orange, Plate 3. Outer petals—Empire Yellow, Plate 4, lightly overcast with Orange Buff, Plate 3. Base of petals—Light Green Yellow, Plate 5. Inside of petals—Light Orange Yellow, Plate 3, lightly overcast with Capucine Yellow, Plate 3. Reverse of petals—Buff Yellow, Plate 4, lightly overcast with Picric Yellow, Plate 4.

*Petals.*—Texture—stiff. Form—long.

*Fragrance.*—Characteristic chrysanthemum.

PLANT

Form: Compact.
Growth: Free.
Foliage:

*Size.*—Large.

*Quantity.*—Normal.

*Color.*—Upper side—Dark Cress Green, Plate 31; reverse side—Light Hellebore Green, Plate 17.

*Texture.*—Leathery; thick.

I claim:

A new and distinct variety of chrysanthemum plant of the hardy decorative type, substantially as herein shown and described, characterized particularly as to novelty by its very compact habit of plant growth, its very healthy, deep Green foliage which remains on the plant all the way to the ground, its stiff, upright stems, its good flower productivity, its large, decorative type and frost resistant flowers, and the distinctive Light Orange Yellow, lightly overcast with Capucine Yellow, general color tonality of its flowers.

No references cited.